US006919209B1

(12) United States Patent
Chatterjee et al.

(10) Patent No.: US 6,919,209 B1
(45) Date of Patent: Jul. 19, 2005

(54) METHOD OF GENETICALLY MODIFYING VERY PRIMITIVE QUIESCENT HUMAN HEMATOPOIETIC STEM CELLS

(75) Inventors: Saswati Chatterjee, Sierra Madre, CA (US); Kamehameha K. Wong, Jr., Sierra Madre, CA (US); Christie Wong, Pasadena, CA (US); Grace Fisher-Adams, La Canada, CA (US)

(73) Assignee: City of Hope, Duarte, CA (US)

( * ) Notice: Subject to any disclaimer, the term of this patent is extended or adjusted under 35 U.S.C. 154(b) by 0 days.

(21) Appl. No.: 09/453,801

(22) Filed: Dec. 3, 1999

Related U.S. Application Data

(60) Provisional application No. 60/111,017, filed on Dec. 4, 1998.

(51) Int. Cl.[7] .................. C12N 15/86; C12N 15/09; C12N 15/00; C12N 5/00; C07H 21/04
(52) U.S. Cl. .................. 435/456; 435/455; 435/325; 435/366; 435/372; 435/375; 435/6; 435/320.1; 536/23.1
(58) Field of Search ................ 435/456, 455, 435/325, 366, 372, 375, 6, 320.1; 536/23.1

(56) References Cited

U.S. PATENT DOCUMENTS 5,474,935 A   12/1995   Chatterjee et al. ....... 435/320.1

FOREIGN PATENT DOCUMENTS

WO           9608560 A    3/1996

OTHER PUBLICATIONS

Luhovy et al. Biology of Blood and Marrow Transplantation. 1996, vol. 2, pp. 24–30.*
Zhou et al. J. Exp. Med. 1994, vol. 179, pp. 1867–1875.*
Fisher–Adams et al. Blood. 1996, vol. 88, No. 2, pp. 492–504.*
Blood. Nov. 1998, vol. 92, No. 10, Supplement 1, Abstract #2738.*
Cheng, Linzhao, et al., "Sustained Gene Expression in Retrovirally Transduced, Engrafting Human Hematopoietic Stem Cells and Their Lympho–Myeloid Progency," *Blood* 92(1):83–92, 1998.
Lusky, Barry D., et al., "Stem Cell Factor, Interleukin–3, and Interleukin–6 Promote Retroviral–Mediated Gene Transfer Into Murine Hematopoietic Stem Cells," *Blood* 80(2):396–402, Jul. 15, 1992.
Verhasselt, Bruno, et al., "Retrovirally Transduced CD34++ Human Cord Blood Cells Generate T Cells Expressing High Levels of the Retroviral Encoded Green Fluorescent Protein Marker in Vitro," *Blood* 91(2):431–440, Jan. 15, 1998.
Chatterjee et al., "Transduction of Primitive Human Marrow and Cord Blood–Derived Hematopoietic Progenitor Cells With Adeno–Associated Virus Vectors," *Blood* 93:1882–1894 (1999).
Kaplitt et al., "Long–Term Gene Expression and Phenotypic Correction Using Adeno–Associated Virus Vectors in the Mammalian Brain," *Nature Genetics* 8:148–153 (1994).
Peel et al., "Efficient Transduction of Green Fluorescent Protein in Spinal Cord Neurons Using Adeno–Associated Virus Vectors Containing Cell Type–Specific Promotors," *Gene Therapy* 4(1):16–24 (1997).

(Continued)

*Primary Examiner*—Gerry Leffers
(74) *Attorney, Agent, or Firm*—Rothwell, Figg, Ernst & Manbeck, P.C.

(57) ABSTRACT

This invention relates to a method for transducing extremely primitive hematopoietic stem cells with high efficiency, using an adeno-associated vector. This vector stably transforms highly primitive CD34$^{+++}$CD38$^-$ cells which reside in a quiescent state and retain to a larger extent the ability to repopulate the hematopoietic system.

11 Claims, 7 Drawing Sheets

OTHER PUBLICATIONS

Wu et al., "Adeno–Associated Virus Vector–Mediated Transgene Integration into Neurons and Other Nondividing Cell Targets," J. Virol. 72:5919–5926 (1998).

Lalwani et al., "Development of in Vivo Gene Therapy for Hearing Disorders: Introduction of Adeno–Associated Virus into the Cochlea of the Guinea Pig," Gene Therapy 3:588–592 (1996).

All et al., "Gne Transfer into the Mouse Retina Mediated by an Adeno–Associated Viral Vector," Human Molecular Genetics 5:591–594 (1996).

Zeitlin et al., "Alveolar Stem Cell Transduction by an Adeno–Associated Viral Vector," Gene Therapy 2:623–631 (1995).

Flotte et al., "Adeno–Associated Virus Vector Gene Expression Occurs in Nondividing Cells in the Absence of Vector DNA Integration," Am. J. Respir Cell Mol. Biol. 11(5):517–521 (1994).

Xiao et al., "Efficient Long–Term Gene Transfer into Muscle Tissue of Immunocompetent Mice by Adeno–Associated Virus Vector," Journal of Virology 70:8098–8108 (1996).

Kessler et al., "Gene Delivery to Skeletal Muscle Results in Sustained Expression and Systemic Delivery of a Therapeutic Protein," Proc. Natl. Acad. Sci. USA 93:14082–14087 (1996).

Fisher et al., "Recombinant Adeno–Associated Virus for Muscle Directed Gene Therapy," Nature Medicine 3:306–312 (1997).

Inouye et al., "Potent Inhibition of Human Immunodeficiency Virus Type 1 in Primary T Cells and Alveolar Macrophages by a Combination Anti–Rev Strategy Delivered in an Adene–Associated Virus Vector," Journal of Virology 71:4071–4078 (1997).

Kaplitt et al., "Long–Term Gene Transfer in Porcine Myocardium After Coronary Infusion of an Adeno–Associated Virus Vector," Am. Thorac. Surg. 62:1669–1676 (1996).

Brenner et al., "Gene–Marking to Trace Origin of Relapse After Autologous Bone–Marrow Transplantation," Lancet 341:85–86 (1993).

McCown et al., "Differential and Persistent Expression Patterns of CNS Gene Transfer by an Adeno–Associated Virus (AAV) Vector," Brain Research 713:99–107 (1996).

Zhou et al., "Adeno–Associated Virus 2–mediated High Efficiency Gene Transfer into Immature and Mature Subsets of Hematopoietic Progenitor Cells in Human Umbilical Cord Blood," J. Exp. Med. 179:1867–1875 (1994).

Chatterjee et al., "Dual–Target Inhibition of HIV–1 in Vitro by Means of an Adeno–Associated Virus Antisense Vector," Science 258:1485–1488 (1992).

Wong et al., "Gene Transfer into Quiescent CD34+CD38– Hematopoietic Progenitor Cells with Adeno–Associated Virus Vectors," Blood 92(10), Suppl. 1, Abstract #2738 (1998).

Luhovy et al., "Stable transduction of recombinant adeno–associated virus into hematopoietic stem cells from normal and sickle cell patients," Biology of Blood and Marrow Transplantation 2:24–30 (1996).

Neering et al., "Transduction of Primitive Human Hematopoietic Cells With Recombinant Adenovirus Vectors," Blood 88(4):1147–1155 (1996).

International Search Report dated Apr. 19, 2000 for copending PCT/US99/28539, filed Mar. 12, 1999.

* cited by examiner

METHOD OF GENETICALLY MODIFYING VERY PRIMITIVE QUIESCENT HUMAN HEMATOPOIETIC STEM CELLS

CROSS-REFERENCE TO RELATED APPLICATIONS

This application claims the benefit of U.S. Provisional Application No. 60/111,017, filed Dec. 4, 1998.

STATEMENT REGARDING FEDERALLY SPONSORED RESEARCH

This invention was made with Government support in the form of Grant Nos. AI-R 014001 and AI-V 193852 from the United States Department of Health and Human Services, NIAID/NIH, and Grant Nos. CA-R0171947, CA-P0159308, CA-P0130206 and CA33572 from the United States Department of Health and Human Services, NCI/NIH. The Government may have certain rights in the invention.

TECHNICAL FIELD

This invention is related to the field of the transfer of genes into hematopoietic stem cells.

DESCRIPTION OF THE BACKGROUND ART

The transfer of therapeutic genes into hematopoietic stem cells (HSC) offers the potential for effective and permanent treatment of a wide spectrum of gene-based diseases including inherited metabolic diseases, viral infections, and cancer. The hematopoietic system is comprised of a hierarchy of cells with different capacities to regenerate all the cells of the blood and bone marrow. Transfer of genes into the most primitive cells (i.e., those most capable of reconstituting the hematopoietic system) is important to the success of genetic therapies. While many studies have evaluated gene transfer into CD34 cells, transduction of stem cells which reside in a quiescent, mitotically dormant, highly primitive state has been difficult to achieve. Despite promising results in vitro, and in murine models, the results of retroviral human gene therapy trials to date have revealed disappointingly low gene transfer frequencies into pluripotent long term repopulating cells. While lentivirus vectors may offer one alternative, their inability to integrate in quiescent cells in addition to safety issues make it imperative to develop other approaches of stable gene transfer into this important cell population.

Despite the widespread use of retrovirus vectors in the majority of human gene therapy trials currently underway, several limitations remain. Human trials and nonhuman primate models of hematopoietic progenitor cell transplantation suggest that the efficiency of retroviral gene transfer into hematopoietic cells is quite low. Results of clinical gene therapy trials utilizing transplantation of retrovirus vector-transduced CD34 cells derived from either bone marrow, cord blood or mobilized peripheral blood, have been informative in determining the potentials of retroviral transduction of human hematopoietic stem cells in vivo. The majority of the results suggest a long term marking frequency of only approximately 1:10,000–1:100,000.

High retroviral transduction frequencies of hematopoietic progenitor cells in vitro, with colony forming unit (CFU) assays and long term culture initiating cell (LTC-IC) assays have been reported. But while gene transfer with retrovirus vectors in lineage-committed CFU have been successful, these studies have not been predictive of in vivo results. Moreover, murine studies showing efficient retroviral transduction of long term hematopoietic repopulating cells did not correlate with large animal models and human gene therapy trials. This discrepancy between the levels of retroviral transduction of human hematopoietic cells in vitro and in vivo is likely attributable to the cell cycle status of the cells at the time of transduction.

Retrovirus vectors pseudotyped with the VSV G protein were found to infect but not integrate into $CD34^+38^-$ cells shown to exist in a nondividing state for at least 72 hours in culture. This suggests that a CD mitotic block rendered these cells untransducable by retroviruses. $CD34^+38^-$ cells which gave rise to CFU only after 60–100 days in culture on stromal layers in extended LTC-IC assays were found to be both quiescent and refractory to retroviral transduction.

Transplantation of retrovirus transduced human CD34 cells in beige/nude/xid (bnx) mice resulted in the detection of common integration patterns in T lymphoid and myeloid lineages, suggesting transduction of a common progenitor. However, the frequency was again very low, with only three common T and myeloid integrants being detected from 24 mice, each transplanted with $10^6$ transduced cells. In addition, prolonged cytokine stimulation of originally cytokine non-responsive primitive progenitor cells was necessary for retroviral transduction.

Non-lentiviral retroviruses require mitosis-induced nuclear membrane breakdown for entry into the nucleus and subsequent viral integration. Primitive hematopoietic progenitor cells induced into cell division by cytokine stimulation are transducable with retrovirus vectors, as are the majority of LTC-ICs, however there is much evidence to suggest that pluripotent hematopoietic stem cells which are required for long term multilineage reconstitution of the hematopoietic system reside primarily in the G0 phase of the cell cycle, with only a few clones dividing at any given time.

Hematopoietic stem cells may be induced to initiate mitosis by exposure to cytokines, but cytokines also induce differentiation. Thus, using this method, the resultant genetically modified cells are no longer pluripotent cells capable of self-renewal and multilineage differentiation. Recent data also suggest that other factors such as a paucity of retrovirus receptors and blocks to reverse transcription may play additional roles in the inability of retroviruses to transduce primitive hematopoietic progenitor cells. Thus, the continued search for other vectors for the safe, stable and efficient introduction of transgenes into hematopoietic stem cells is imperative.

Pluripotent human hematopoietic stem cells with the capacity to self-renew and give rise to progeny of all hematopoietic lineages, including lymphoid, myeloid and erythroid cells, may be purified from either cord blood, bone marrow or mobilized peripheral blood. Immunophenotypic analysis reveals that hematopoietic stem cells are contained within the $CD34^+$ compartment of hematopoietic cells. Further subdivision reveals that pluripotent human hematopoietic stem cells are $CD38^-$, lack lineage-specific differentiation markers and exclude Rhodamine 123. Cells possessing these characteristics are very primitive, highly pluripotent, mitotically quiescent and maintain a minimal level of metabolic activity.

Recent studies defined non-dividing CD34 cells as G0 on the basis of their low RNA and DNA content. Gothot t al., *Blood* 90(11):4384–4393 (1997); Ladd e al., *Blood* 90(2): 658–668 (1997); Gothot et al., *Exp. Hematol.* 26(7): 562–570 (1998); Donnelly et al., *Exp. Hematol.* 27(5): 788–796 (1999). Some of these G0 CD34 cells have been shown to remain cytokine nonresponsive for at least seven days in culture with cytokines and to be enriched in extended long-term culture-initiating cell assays (LTC-IC). LTC-IC assays are well-known in the art. However, culture conditions that allow prolonged hematopoietic stem cells survival and self-renewal are as yet undefined. As discussed above, the cytokines that normally are added to stem and progenitor cell cultures to maintain viability, also induce undesired lineage commitment and differentiation.

The lack of appropriate direct assay systems to test self-renewing pluripotential human stem cells in vitro also has impeded attempts to analyze gene transfer into this population. Short term CFU assays test the ability of progenitor cells to divide and differentiate into lineage-specific colonies and primarily measure committed late-stage progenitors but not stem cells. Long term marrow stroma cultures with a hematopoietic microenvironment capable of supporting hematopoiesis for five weeks or longer have been described. Southerland et al., *Blood* 74:1563 (1989). In these cultures, more primitive colony forming cells (CFC) can survive five weeks or longer and still retain the capacity to differentiate late in culture.

While LTC-IC bear some correlation to long-term repopulating cells in animal models and are enriched in immunophenotypic compartments which are also enriched for stem cells, gene marking studies indicate that LTC-IC do not represent the pluripotent hematopoietic stem cells capable of long term lympho-myeloid reconstitution. However, this assay is still used extensively to measure primitive myelo-erythroid progenitor activity.

Extended LTC-IC have been described which measure the ability of primitive $CD34^+38^-$ cells to give rise to CFCs after 60 days of culture on a radiated stroma layer. Hao et al., *Blood* 88:3306–3313 (1996). These cells have been shown to possess mitotic and immunophenotypic characteristics of very primitive progenitor cells.

Attempts also have been made to test human hematopoiesis in immunodeficient mice. Cell populations containing hematopoietic stem cells have been transplanted into mice bearing the severe combined immuno deficiency (SCID) mutation (rag2−/−) or beige/nude/xid (bnx) mutations. SCID mice lack mature T or B cells but have elevated levels of natural killer (NK) cells and serum complement and with age develop leakiness in the B cell compartment. While engraftment of human hematopoietic cells have been observed in SCID mice that have been provided with either human bone/thymus/liver grafts or human cytokines, the levels of engraftment are low. It is postulated that in SCID mice the elevated levels of NK cells are responsible for natural resistance to marrow grafts and the presence of serum complement contribute to low levels of human engraftment. Bnx mice, which lack functional B, T and NK cells, show somewhat improved levels of engraftment with these cells.

Recently, the SCID mutation was back-crossed onto the non-obese diabetes (NOD/Lt) background (NOD/SCID). Shultz et al., *J. Immunol.* 154:180 (1995). These mice have multiple defects in adaptive and innate immunity with no functional mature T or B lymphocytes, no NK cells, no complement, and defective macrophage function. They support engraftment of human hematopoietic cells better than SCID or bnx mice. Human CD34 cells engrafted in NOD/SCID mice home to the bone marrow where B lymphopoiesis, myelopoiesis, and erythropoiesis occur. Human hematopoiesis in the NOD/SCID mice is accompanied by the continued production of self-renewing $CD34^+$ progenitors, colony-forming cells (CFC) and cells capable of giving rise to hematopoiesis upon serial transplantation. CFC present in the marrow of human engrafted NOD/SCID mice up to is ten weeks post transplantation were shown by thymidine suicide studies to be derived from quiescent cells. Therefore, NOD/SCID mice provide a model for the analysis of gene transfer into quiescent human hematopoietic stem/progenitor cells and a better predictor of successful genetic therapy for human disease.

Lentivirus vectors have recently gained attention for their ability to transduce non-dividing cells and pseudotyped lentivirus vectors have been shown to infect $CD34^+$ cells. However, the majority of the transduced non-dividing cells were either in G1 or G2. A recent study reports that despite evidence of entry of certain lentivirus vectors into non-dividing $CD34^+38^-$ cells, stable integration and transgene expression could not be detected. Therefore, despite the ability of lentiviruses to enter the nuclei of non-dividing cells, other factors may pose significant impediments to gene transfer into stem cells in the G0 phase of the cell cycle using these types of vectors. Additionally, there are significant safety concerns regarding the use of lentivirus vectors in clinical trials, especially for diseases other than HIV infection.

For stem cell gene therapy to become an effective therapeutic modality, higher levels of gene transfer in hematopoietic stem cells must be attained. AAV vectors are attractive vehicles since they (1) transduce $CD34^+$ and $CD34^+38^-$ cells, (2) transduce non-dividing cells, (3) show chromosomal integration, (4) do not encode viral genes and are not highly immunogenic, and (5) are non-pathogenic.

Adeno-associated virus (AAV, a parvovirus), is a single-stranded replication-defective DNA virus with a 4.7 kb genome having palindromic inverted terminal repeats (ITR) which are important for viral integration. Co-infection with a helper virus, typically adenovirus or herpes simplex virus, is required for productive infection. In the absence of helper virus co-infection, AAV stably and efficiently integrates via the ITRs into cellular DNA. DNA to be transferred using AAV must be contained within the AAV ITRs. Latent wild-type AAV infections have been stably maintained in tissue culture for greater than 100 serial passages in the absence of selective pressure, attesting to the stability of AAV genomic integration. AAV vectors have demonstrated high transduction frequencies in cells from diverse species (chickens to primates) and in lineages including those of hematopoietic origin.

Other advantages to AAV transduction include the fact that DNA polymerase, the enzyme responsible for AAV replication, has increased fidelity as compared to reverse transcriptase, which has a 100–10,000 fold higher error frequency. In addition, wild-type AAV has yet to be definitively identified as a pathogen in either animals or humans. On the contrary, there is evidence that infection with wild-type AAV inhibits transformation by papilloma viruses and activated H-ras oncogene in vitro. In addition, epidemiological studies suggest that prior infections in humans may confer oncoprotection. Moreover, AAV vectors which do not encode viral genes have been shown to have low immunogenicity, and prolonged in vivo transgene expression from AAV vectors has been documented.

The use of an AAV vector to deliver an antisense gene targeting the RNA sequences present in the 5'- and 3'-regions of HIV-1 mRNA has been described (Chatterjee et al., *Science* 258:1485–1488 (1992). Transduced cells showed specific and significant inhibition of HIV LTR-directed gene expression and virus replication. AAV transduction was not associated with any toxicity or alterations of cell viability, growth inhibition or heterologous transcription. This study represented the first use of an AAV-based anti-HIV vector. See also U.S. Pat. No. 5,474,935, which describes AAV vectors based on CWRSV and their use to transfer genes to bone marrow cells.

AAV vectors encoding ribozymes to HIV and viral-transforming genes have been developed. AAV vectors have been used to express the human tyrosine hydroxylase II gene, factor IX, neuropeptide Y, human glucocerebrosidase and arylsulfatase A, the CFTR gene, beta globin and antisense to alpha globin. Studies have been published showing AAV transduction of primary non-dividing cells, for example, post-mitotic neurons in vivo, olfactory tubercle, piriform cortex and multipolar neurons, cochlear cells, retinal cells, glial cells of the human central nervous system, non-proliferating respiratory epithelial cells, alveolar stem cells, adult skeletal muscle, cardiac muscle, noncycling tumor cells and primary human peripheral blood monocyte-macrophages.

It previously has been shown that AAV vectors can transduce non-dividing cells, for example smooth muscle cells and neurons, both in vivo and in vitro. There also have been recent demonstrations of the capacity of AAV vectors to transduce clonogenic $CD34^+$ and $CD34^+/CD38^-$ human hematopoietic progenitor cells and to display chromosomal integration. Fisher-Adams et al., *Blood* 88:492 (1996); Chatterjee et al., *Blood* 92:1882 (1999). Successful genetic transformation of extremely primitive $CD34^{+++}/CD38^-$ cells which demonstrably are in the G0 phase of the cell cycle has not previously been shown.

The capsid proteins comprising AAV virions possess nuclear localization signals, which facilitate their entry through the nuclear pores of non-dividing cells. Wild type AAV is unique among eukaryotic viruses in its ability to integrate site-specifically into the AAVS 1 site of the human chromosome 19. This integration is mediated by the virus-encoded rep78 protein which recognizes consensus sequences on both the AAV LTR and AAVS1. Rep78 possesses site specific, DNA-binding, endonuclease and helicase activities and is postulated to form a bridge between the wild type AAV genome and AAVS1 to facilitate site-specific integration. Rep-free, wild type-free AAV vectors, however, do not integrate into AAVS1.

Gene transfer vectors based on adeno-associated virus (AAV) appear promising because of their high transduction frequencies regardless of cell cycle status and ability to integrate into chromosomal DNA. The ability to insert transgenes into pluripotent hematopoietic stem cells residing in the G0 phase would represent a significant advance in the field of human gene therapy since the ability to deliver genes to the appropriate population of cells has been a major stumbling block until the present time.

AAV vectors have recently been approved for use in clinical gene therapy for cystic fibrosis based on recent observations of long-term in vivo expression of an AAV vector-encoded cystic fibrosis transmembrance conductance regulatory gene in rabbit airway epithelial cells. For clinical applications, the ability to transfer genes efficiently into a large fraction of hematopoietic progenitor cells in the absence of drug selection is highly desirable because the long-term effects of drug selection on the fate of transduced cells in vivo is unknown. There has been no prior disclosure of the transduction of $CD34^+$ cells that were highly primitive, non-dividing cells residing in G0, therefore a significant need remains in the art for methods which can achieve this.

SUMMARY OF THE INVENTION

Accordingly, the present invention provides a method for stably integrating DNA into multi-potential hematopoietic stem cells in the G0 phase of the cell cycle (e.g., a non-dividing, quiescent phase), by transducing with an adeno-associated virus vector containing the DNA. In a preferred embodiment, the invention provides a method for stably transferring DNA into $CD34^{+++}CD38^-$ hematopoietic stem cells in the G0 phase of the cell cycle by transducing such cells with an adeno-associated virus vector based on the CWRSV backbone or selected from vCWRHIVAPAP, vCWIHIVASVN and vCWRAP and maintaining such cells under conditions such that the cells in the phase do not differentiate or undergo mitosis substantially during the transduction process. The invention also provides adeno-associated virus vectors which stably transfer DNA into multi-potential hematopoietic stem cells residing in the G0 phase of the cell cycle and stably transduced multi-potential hematopoietic stem cells residing in the G0 phase of the cell cycle.

DETAILED DESCRIPTION OF THE PREFERRED EMBODIMENTS

Figure 1:
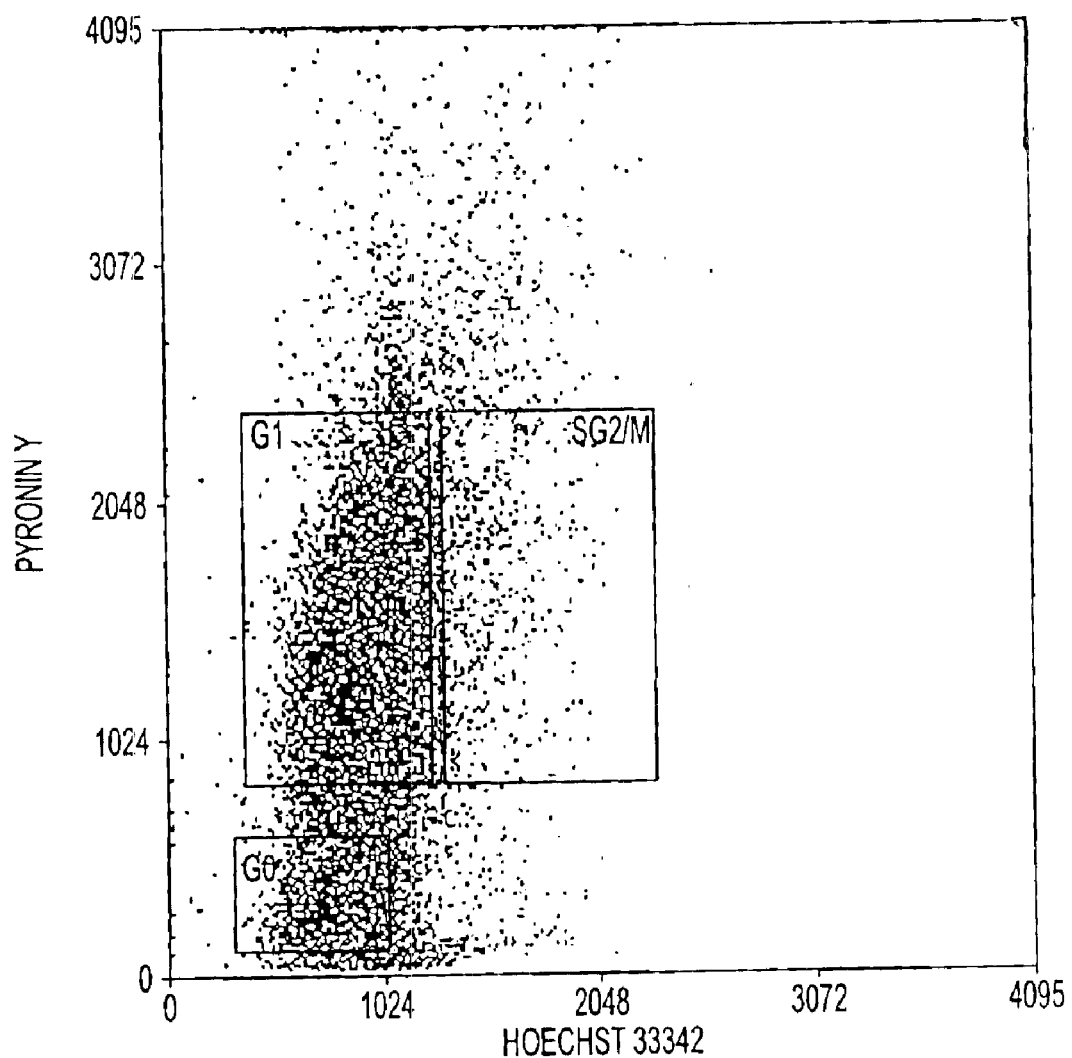
FIG. 1 shows fluorescence activated cell sorting (FACS) results from a CD34 cell population stained with a combination of the vital dyes Hoechst 33342 and Pyronin Y. The cells were sorted based on DNA and RNA content, respectively. The boxes marked G0, G1 and SG2/M indicate the cells defined as residing in that phase of the cell cycle.

The present invention provides methods and vectors which enable transfer of DNA to cells which are in the G0 phase of the cell cycle, and remain in a non-differentiated, non-dividing state during the transduction process. Under the conditions of the method, in particular, low cytokine levels, hematopoietic stem cells in culture remain quiescent and mitotically dormant for up to 2 days (48 hours) or even longer. Of course, the longer the cells remain in culture, the more cells in the population will begin to divide. It is preferred, therefore to use a transduction time of 48 hours or less, generally about 2 hours to about 48 hours. More preferably, a transduction time of about 2 hours to about 24 hours is used. A transduction time of about 18 to about 24 hours is most preferred.

In order to perform the method, low cytokine (IL-3, IL-6 and granulocyte-macrophage colony stimulation factor (GMCSF) levels are important. The higher the cytokine levels the more the cells are stimulated to undergo mitosis. Too low a level can result in cell death, however. Using the inventive method, it is therefore advantageous to use cytokine levels of no greater than about 15 ng/ml IL-3, 15 ng/ml IL-6 and 1.5 ng/ml granulocyte macrophage colony stimulating factor. Preferably levels between 1–15 ng/ml IL-3, 1–15 ng/ml IL-6 and 0.1–1.5 ng/ml GMCSF. More preferably, cytokines are present at 5–10 ng/ml IL-3, 5–10 ng/ml IL-6 and 0.5–1 ng/ml GMCSF. The most preferred cytokine levels are 10 ng/ml IL-3, 10 ng/ml IL-6 and 1 ng/ml GMCSF.

The inventive method allows the cells to remain in G0 during transduction, resulting in stable integration of transferred DNA into the genome of quiescent multi-potential hematopoietic stem cells. The integration is stable for at least 4 weeks or 8 weeks, or much longer. Preferably, the hematopoietic stem cells are highly primitive cells such as $CD34^{+++}CD38^-$ cells.

AAV vectors contain the DNA to be transferred. Such vectors are most useful if the DNA is contained within the adeno-associated virus inverted terminal repeats and if the virus vector is encapsidated. Particularly useful vectors are derived from the base vector CWRSV. The vector may contain a wild-type polyadenylation region. Most preferred vectors include vCWRHIVAPAP, vCWRHIVASVN CWRHIVASVA, and vCWRAP.

Any DNA may be transferred with the inventive method, including entire genes, gene fragments, recombinant genes or DNA fragments, antisense DNA or any desired DNA. Marker genes and reporter genes also may be transferred.

The vectors of the present invention stably transfer DNA into multi-potential hematopoietic stem cells which reside in the G0 phase of the cell cycle. The cells substantially remain in G0 for at least about 2 days or up to about 7 days, or longer. After about 7 days in culture, greater than 80% of the transduced stem cells can remain in G0. Generally, cells of the invention are about 92 to 99% non-dividing after about 2 days and about 65% to about 83% non-dividing after about 7 days of culture. Thus, the cells do not differentiate at an appreciable rate.

AAV vectors have been demonstrated to transduce very primitive, highly pluripotent progenitor cells ($CD34^{+++}$ $CD38^-$ cells) capable of long term engraftment. The cells were purified from CD34 cells of bone marrow, peripheral blood or cord blood and are hereinafter referred to as "stem cells" or "hematopoietic stem cells." Gene transfer of the human placental alkaline phosphatase (PLAP) gene by AAV vectors was readily observed in long term culture over a period of 10 weeks. Transduction was observed in every donor analyzed. Importantly, transgene transcription and expression was observed in the-absence of selective pressure. This invention therefore provides a method for stably transferring DNA into non-dividing, quiescent, multi-potential hematopoietic stem cells, including cells which reside in G0, using adeno-associated virus vectors.

Hematopoietic stems cells were obtained from bone marrow, peripheral blood or umbilical cord blood. Bone marrow samples were obtained from healthy donors for allogeneic transplant recipients following informed consent and using an Institutional Review Board-approved protocol. Umbilical cord blood was procured from Huntington Memorial Hospital, Pasadena, Calif., using a protocol approved by Institutional Review Boards. Unless otherwise noted, cells were cultured in RPMI 1640 or Iscove's modified Dulbecco's medium containing 20% heat-inactivated fetal calf serum, 2 mM L-glutamine, 100 U/ml penicillin, and 100 mg/ml streptomycin with specific cytokines (10 ng/ml IL-3, R&D Systems, Minneapolis, Minn.; 5 ng/ml IL-6, R&D Systems; and/or 1 ng/ml granulocyte-macrophage colony stimulating factor (GM-CSF), R&D Systems) at 37° C. in humidified 5% $CO_2$. Light density mononuclear cells were separated by Ficoll-Hypaque centrifugation (Pharmacia, Piscataway, N.J.). After three washes with phosphate-buffered saline (PBS), cell and viability counts were performed and cells were resuspended in PBS with 0.5% BSA and 2 mM EDTA before use.

The $CD34^+$ population of bone marrow cells was immunomagnetically purified from mononuclear cells using CD34 isolation kits (Miltenyi Biotech, CA) following the manufacturer's directions. CD34 cells were passed through two columns sequentially to increase purity and enrich for $CD34^{+++}$ cells. CD34 purity was 96–98% as assessed by flow cytometry following direct immunolabeling with fluorescein isothiocyanate (FITC)-conjugated HPCA-2.

$CD34^+38^-$ cells were cytofluorometrically sorted using a Mo-Flo high flow cytometer (Cytomation, Ft. Collins, Colo.) following labeling with FITC-conjugated anti-CD34 (anti-CD34 FITC) and phycoerythrin-conjugated anti-CD38 (anti-$CD38^-$PE) (Becton Dickinson, San Jose, Calif.). Enriched total CD34 cells were stained according to procedures known in the art with a combination of the vital dyes Hoechst 33342 and Pyronin Y to identify cell types. The dyes allow fluorescence-activated cell sorting based on DNA and RNA content, respectively. This live cell staining followed by flow cytometric sorting was used to purify CD34 cells in the G0 phase of the cell cycle. Skilled artisans will recognize various methods which are also suitable to obtain highly primitive G0 cells for transfection.

Figure 2B:
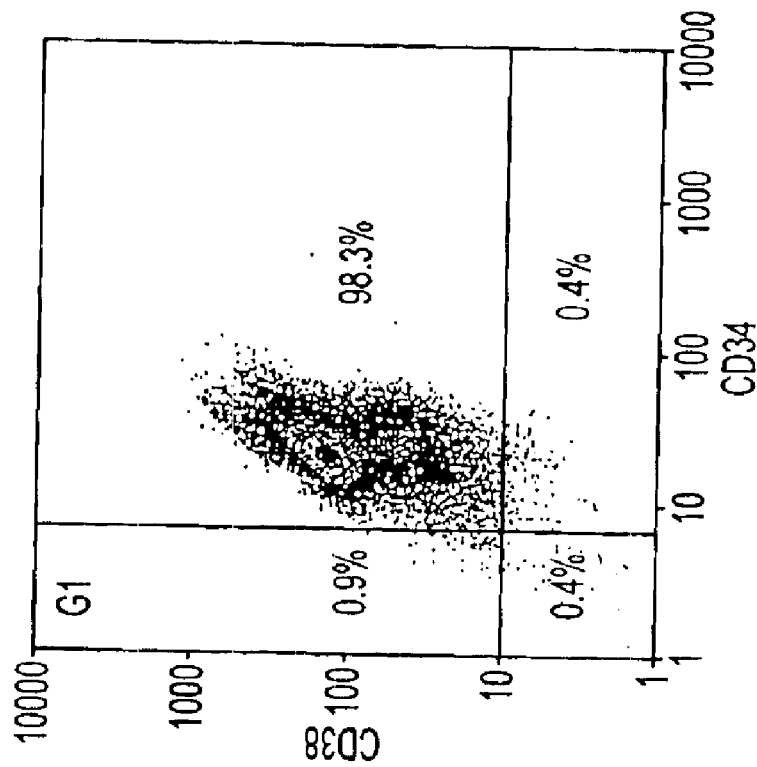
FIG. 2 shows the CD34 and CD38 antigen expression or G0 (FIG. 2A) and G1 (FIG. 2B) sorted cells sorted by FACS.
Figure 2A:
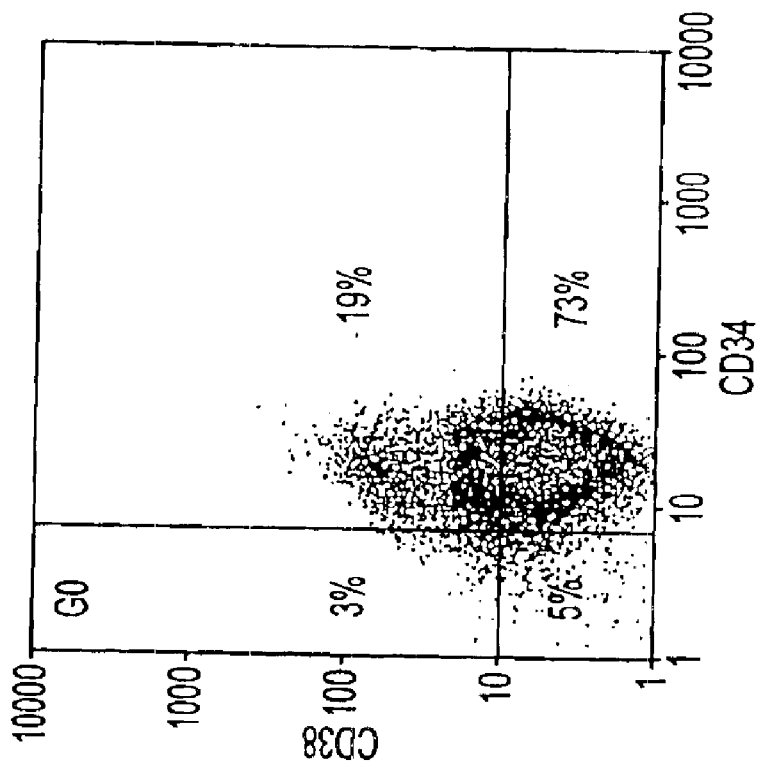

The cell cycle status of bone marrow total CD34 cells were identified as follows. Cells with 2N DNA (low Hoechst 33342) and minimal RNA content (low Pyronin Y) were identified as G0 according to prior art methods. Cells with both 2N DNA (low Hoechst 33342) and accumulation of RNA (high Pyronin Y) were identified as GI. Cells with greater than 2N DNA (high Hoechst 33342) and high RNA (high Pyronin Y) were identified as SG2 or M phase cells. See FIG. 1. G0 and G1 sorted cells were further evaluated for their expression of CD34 and CD38 cell surface antigens by direct immunostaining using monoclonal antibodies as described below. CD34 cells in G0 are largely $CD38^-$. See FIG. 2.

Figure 3:
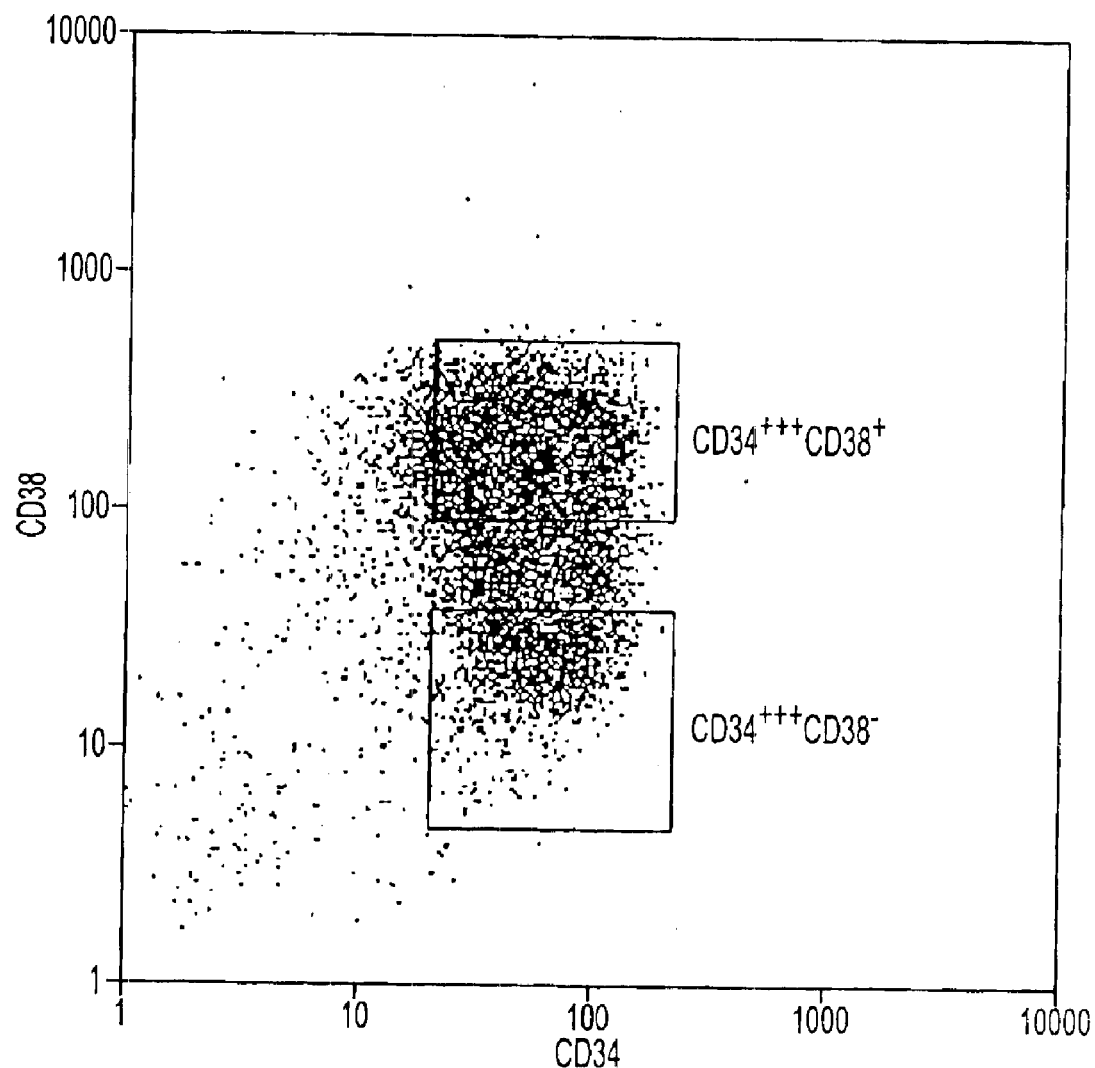
FIG. 3 provides the FACS sorting criteria defined for $CD34^{+++}CD38^-$ cells isolated from bone marrow total CD34 cells.

Enriched total CD34 cells were stained directly with anti-CD34 FITC and anti-CD38 PE monoclonal antibodies according to-methods which are well-known in the art. After staining, the cells were washed twice and analyzed using a Mo-Flo high speed flow cytometer. The defined sorting criteria are shown in FIG. 3. The dimmest 5–10% of the $CD34^{+++}$ cells were sorted as the $CD34^{+++}CD38^-$ population. The isolated cells in the Figure represent the dimmest 6% except for donor OM who was very young. The majority of these cells were in G0, were quiescent and consisted of $CD34^+38^-$ cells, while G1 cells were primarily $CD38^+$.

TABLE 1

Enriched Marrow Total CD34 Cells
Residing in Various Subcompartments
of the Cells Cycle.

| Donor | G0 | G1 | SG2/M |
|---|---|---|---|
| JG | 15.0% | 45.0% | 3.9% |
| DP | 23.0% | 57.5% | 4.8% |
| AA | 32.3% | 27.8% | 3.0% |
| SM | 20.5% | 43.8% | 3.4% |
| AS | 19.0% | 47.2% | 1.2% |

TABLE 4

Cell cycle status of CD34$^{+++}$CD38$^-$ and CD34$^{+++}$CD38$^+$
sorted populations

| Donor | Sorted Population | G0 | G1 | SG2/M |
|---|---|---|---|---|
| OM | CD38$^-$ | 98% | 0.2% | 0.4% |
|  | CD38$^+$ | 21% | 37% | 22% |
| ME | CD38$^-$ | 93% | 0.2% | 4% |
|  | CD38$^+$ | 13% | 2% | 75% |
| RB | CD38$^-$ | 65% | 4% | 27% |
|  | CD38$^+$ | 14% | 20% | 60% |

Figure 4B:
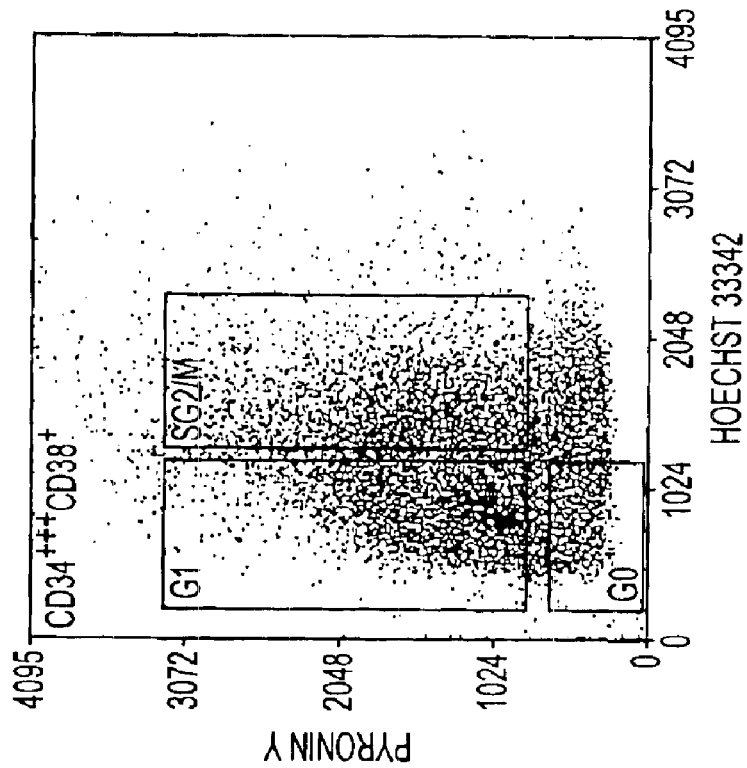
FIG. 4 shows the DNA/RNA content and cell cycle status of sorted $CD34^{+++}CD^-$ (FIG. 4A) and $CD34^{+++}CD13^+$ (FIG. 4B) cells.
Figure 4A:
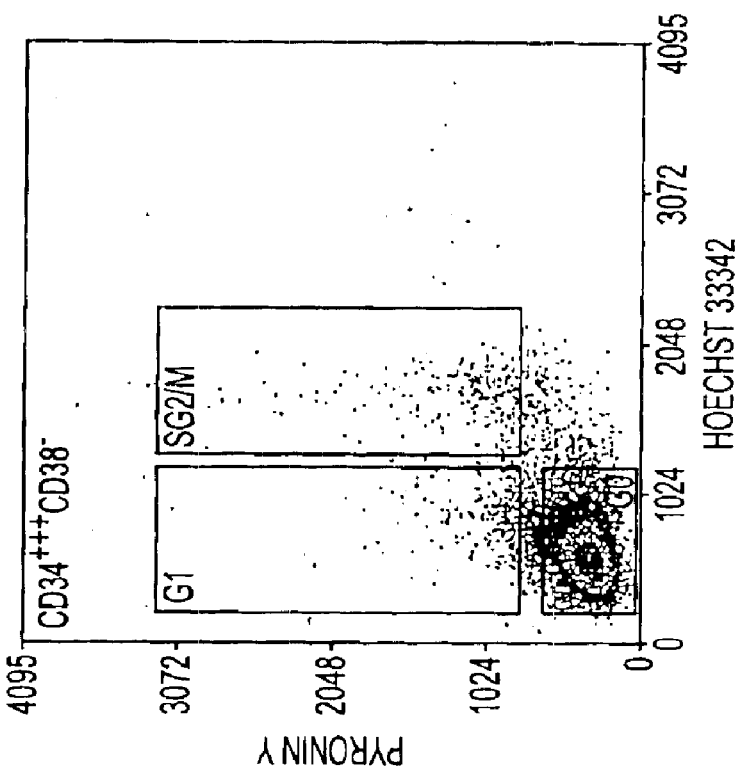
Figure 5A:
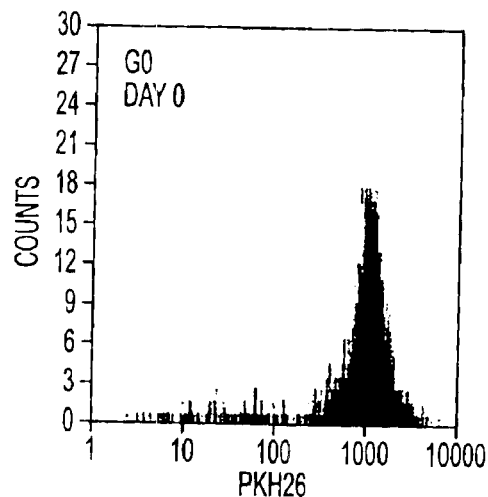
FIG. 5 shows the PKH26 analysis of sorted G0 CD34 (FIGS. 5A, 5C and 5E) and G1 CD34 (FIGS. 5B, 5D and 5F) cells at Day 0 (5A, 5B), Day 1 (5C, 5D), and Day 7 (5E, 5F) of culture in the presence of cytokines.
Figure 5B:
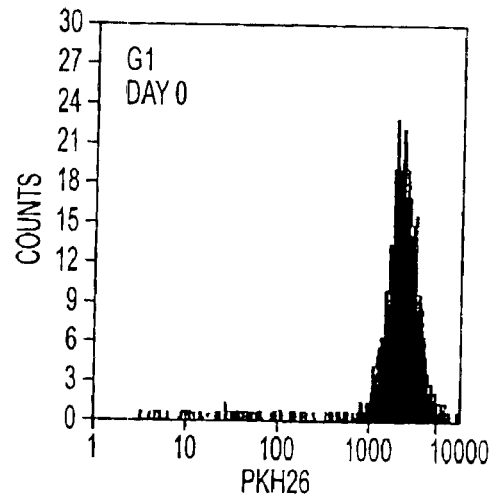
Figure 5C:
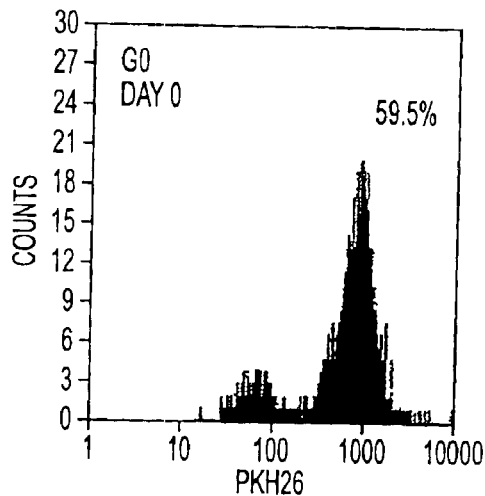
Figure 5D:
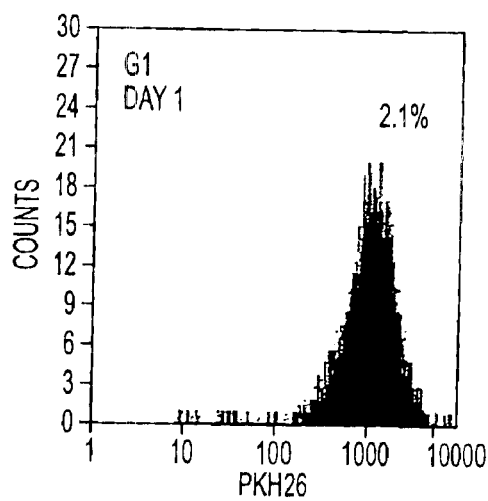
Figure 5E:
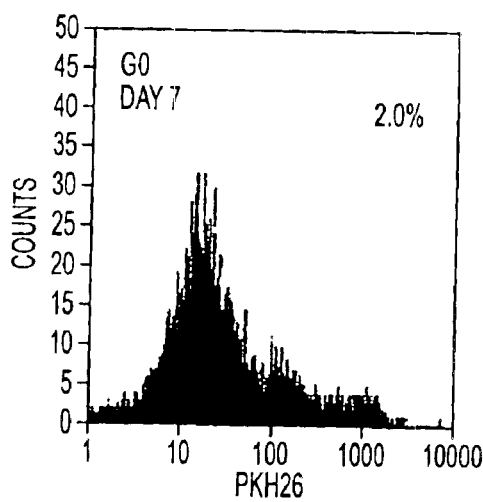
Figure 5F:
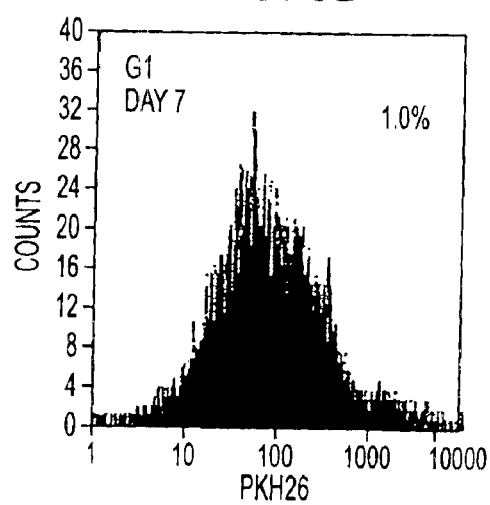
Figure 6A:
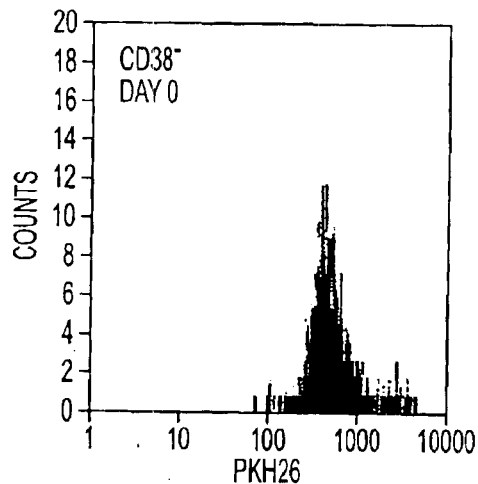
FIG. 6 shows the PKH26 analysis of sorted $CD34^{+++}$ $CD38^-$ (FIGS. 6A, 6C and 6E) and $CD34^{+++}CD38^+$ (FIGS. 6B, 6D and 6E) cells at Day 0 (6A, 6B), Day 7 (6C, 6D), and Day 14 (6E, 6F) of culture in the presence of cytokines.
Figure 6B:
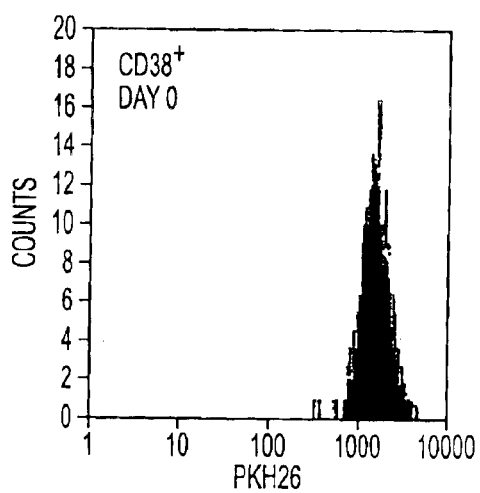
Figure 6C:
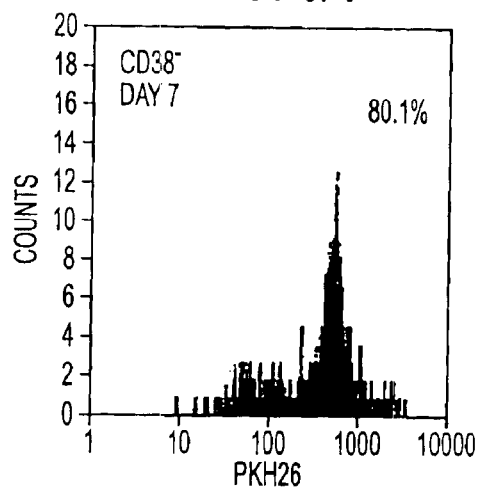
Figure 6D:
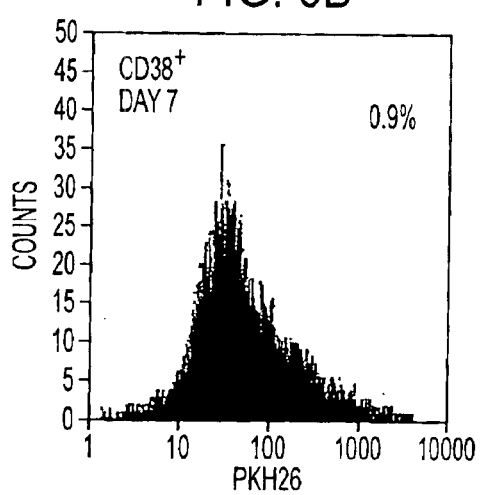
Figure 6E:
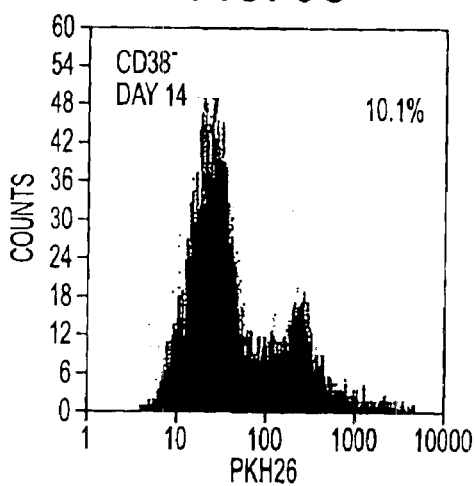
Figure 6F:
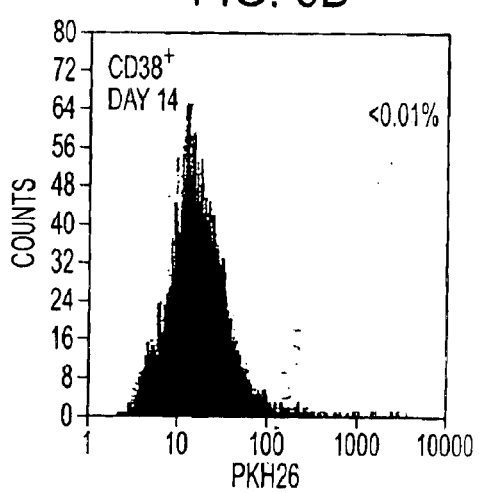

FIG. 4 depicts the cell cycle status of sorted CD34$^{+++}$ CD38$^-$ and CD34$^{+++}$CD38$^+$ cells, determined by sorting based on DNA and RNA content. From the data regarding surface markers, DNA and RNA content and mitotic properties of the total marrow CD34 cells and the sorted CD34 cells, one can conclude that the total CD34$^{+++}$ population generally includes cells at different stages of the cell cycle, but that the majority of enriched CD34 cells generally were found in G1. See FIG. 4 and Table 1. The data in Table 1 show the percentage of enriched marrow total CD34 cells residing in various subcompartments of the cell cycle, by donor. Cells residing in G0 ranged from 15–32% of the marrow total CD34 population. Table 2 gives the percentage of enriched marrow total CD34 cells which are CD34$^{+++}$ CD38$^-$. This percentage averages near 5.7% omitting OM, who was a very young donor. Cells sorted as G0 expressed low levels of CD38 cell surface antigen whereas G1 cells expressed CD38 antigen at least one log higher in intensity compared to G0. Analysis by DNA and RNA content revealed that the CD34$^{+++}$CD38$^-$ cells reside primarily in G0, while CD34$^{+++}$CD38$^+$ cells were mainly in G1 and SG2/M of the cell cycle. See Tables 3 and 4. Note that the majority of cells in G0 are CD38$^-$. See Table 3 and FIG. 2.

TABLE 2

Percentage of CD34$^{+++}$CD38$^-$ Cells from
Enriched Marrow Total CD34 Cells.

| Donor | CD34$^{+++}$CD38$^-$ |
|---|---|
| OM* | 10.6% |
| RL | 4.8% |
| RS | 6.6% |
| ME | 5.6% |

*Young bone marrow donor

TABLE 3

Percentage of G0 and G1 sorted populations
expressing CD34 and CD38 antigenic markers

| Donor | Sorted Population | % CD34$^{+++}$CD38$^+$ | % CD34$^{+++}$CD38$^-$ |
|---|---|---|---|
| JG | G0 | 19% | 73% |
|  | G1 | 98% | 0.4% |
| SM | G0 | 33% | 58% |
|  | G1 | 90% | 3% |
| AS | G0 | 18% | 71% |
|  | G1 | 92% | 2% |

PKH26 is a lipophilic fluorescent dye that stains the membranes of live cells. The fluorescent intensity of the stain halves with each division, allowing quantitation of the number of rounds of mitosis. PKH26 was used to analyze and compare proliferation of different cell populations and to confirm the non-dividing status of the cell population. Other methods will readily occur to the skilled artisan, whereby the G0 status or non-mitotic state can be confirmed. The cells were stained according to known methods. After staining, cells were analyzed by flow cytometry on the initial day of staining and designated as Day 0. Remaining cells were cultured in IMDM containing 20% FCS, IL-3 (10 ng/ml), IL-6 (10 ng/ml), and SCF (1 ng/ml) and cultured for further PKH26 analysis on later days. Flow cytometric raw data was analyzed for quantitative measure of cell proliferation and daughter generations with ModFit software.

Membrane staining with PKH26 showed that CD34 cells in G0 began to proliferate more slowly than cells in G1 in response to low concentrations of cytokines. See FIG. 5. In FIGS. 5 and 6, the signal at Day 0 is defined as 100%. The percentage given for each of the other panels indicates the percentage of signal remaining. Diminished signal indicates a greater amount of cell division in the cultures.

PKH26 also was used to analyze and compare the proliferation of G0 CD34$^{+++}$CD38$^-$ and CD34$^{+++}$CD38$^+$ sorted cells. The data in FIG. 6 indicate that CD34$^{+++}$CD38$^-$ cells continue to be quiescent even after culture in the presence of low concentrations of cytokines. CD34$^{+++}$38$^-$ cells were found to be highly quiescent, with >80% remaining in G0 after extended culture (seven days). Both CD34$^{+++}$38$^-$ and CD34 cells in G0 were found to be enriched for LTC-IC with extended clonogenic capacity while cells in G1 had very limited LTC-IC activity. In the absence of selective pressure, 19–50% of week 5, 8 and 12 LTC-IC from the G0 population of CD34 cells showed evidence of vector sequences while only 11–30% of LTC-IC from cells in G1 were stably transduced (data not shown). See Table 6, below.

Figure 7:
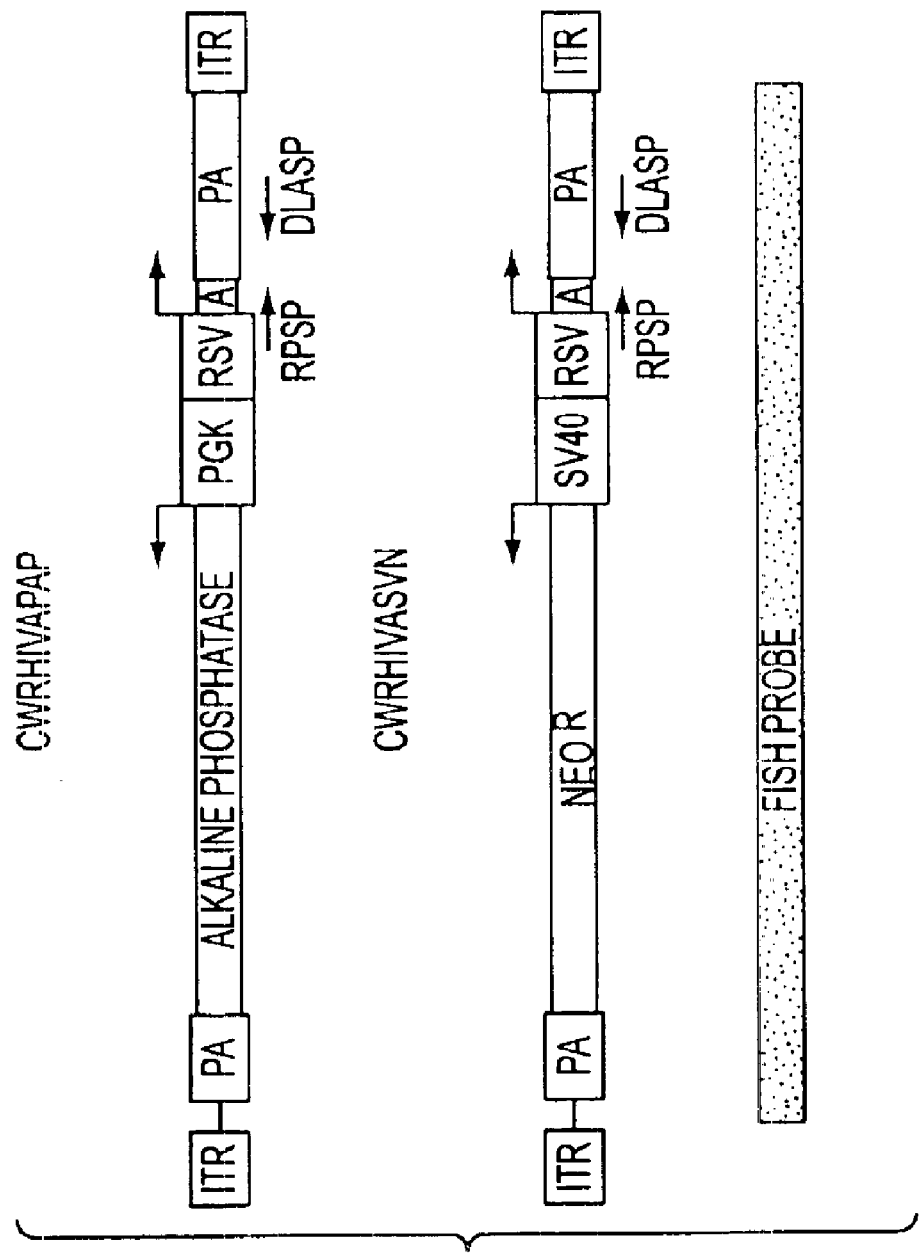
FIG. 7 shows a map of the AAV vectors CWRHIVAPAP and CWRHIVASVN.

These extremely primitive, quiescent CD34 cells (CD34 cells which sorted as CD34$^{+++}$38$^-$ and were gradient purified AAV vectors derived from the base vector CWRSV (Chatterjee 1992 & U.S. Pat. No. 5,474,935) CWRHIVASVN contains a transcriptional cassette encoding the neomycin phosphotransferase (NEO$^R$) gene under SV40 early promotor control and another transcriptional cassette encoding an antisense transcript complementary to HIV-1 LTR sequences under RSV LTR control. CWRHIVAPAP is the same as CWRHIVASVN except the SVNeo cassette has been replaced by a gene cassette encoding the thermostable human PLAP gene under phosphoglycerate kinase (PGK) promotor control. FIG. 7 shows a map of CWRHIVAPAP and CWRHIVASVN.

The location of primers used for the amplification of vector sequences of individual LTC-IC and the 3.6 kb Hpa1/SpaBI fragment derived from pCWRHIVASVN used for FISH analyses are also indicated on the Figure. The AAV based vectors shown in FIG. 7 may be prepared by the method disclosed in U.S. Pat. No. 5,474,935, which is incorporated herein by reference, or by any convenient method. Of course, it is readily apparent to those skilled in the art that many other vectors are suitable for use with the inventive method disclosed here and that they may be prepared by any convenient method. For the exemplary methods here, herpes simplex virus type 1 (HSV-1) MP17 was used as the helper virus for AAV vector encapsidation, and was propagated and titered by plaque assays according to known methods. Transductions were performed by direct addition of vector to the cells, however any suitable transduction method may be used. Only cesium chloride gradient purified vector stocks that were free of wild-type AAV were used for LTC-IC and FISH assays. The particle titer of the vector stocks was $10^{10}$–$10^{12}$ and the infectious titer was $10^8$–$10^{10}$. Those of skill in the art are aware, however, that titers are advantageously adjusted according to conditions, including vector type and transduction method.

Following AAV vector transduction of target cells, the single-stranded genomes converted to the double-stranded form. They may survive either as episomal DNA or integrated in the nucleus of transduced cells. Both episomal and integrated forms have been described for wild type AAV and AAV vectors. Results here suggest that approximately 10–40% of transduced cells may contain integrated vector sequences. rAAV transduction was observed in every donor analyzed in the absence of selective pressure, although a wide range of gene transfer frequencies was noted. Gene transfer frequencies in primitive clonogenic cells within these populations were measured by PCR amplification of vector sequences from individual colonies from LTC-IC assays according to known methods.

Two-color hybridization was performed to determine if the rep-negative, wild-type-free vector stocks used had integrated at sites distinct from AAVS1, the integration site for wild-type AAV. Co-localization of the AAVS1 probe and the vector probe was never observed in any transduced cell (0/100 nuclei) indicating that in the absence of either rep 78 or wild-type AAV, vCWRHIVAPAP did not integrate into AAVS1. Results demonstrated that primitive clonogenic CD34$^+$38$^-$ cord blood cells transduced with AAV vectors demonstrated transgene expression at 8 weeks post transduction in the absence of G418 selection. These findings are consistent with both the analysis of transduction of LTC-IC and FISH analysis of CD34 cells.

AAV vector transduction of long-term bone marrow cultures (LTBMC) was performed as follows. CD34 cells were purified from light density bone marrow or cord blood mononuclear cells and transduced with vCWRHIVAPAP encoding an antisense RNA complimentary to the HIV-1 LTR under the control of the RSV LTR and the gene encoding thermostable human PLAP under the control of the phosphoglycerate kinase promoter at a functional multiplicity of 3 (particle MOI:600). CD34 cells were transduced immediately after isolation and plated in long term culture on a irradiated heterologous stroma along with untransduced controls.

CD34 cells were transduced with vCWRHIVAPAP at a functional MOI:3 (particle MOI:600) on day 0 and plated in long term culture as described above. As discussed above, the transduction time must be limited so that the cells do not begin to appreciably divide or differentiate during this time. Transduction may be carried out for as short a time as about 2 hours, or for as long as about 48 hours. Conveniently, transduction is performed overnight, and generally, transduction begins soon after isolation of the cells. Preferred transduction times are from about 2 hours to about 24 hours and most preferred transduction times are from about 18 hours to about 24 hours. Cells harvested from stromal layers at designated time points were washed and plated in methylcellulose with no G418 selection and colonies were plucked after 2 weeks. No toxicity or major differences in cellularity were observed in transduced cultures as compared to untransduced controls. DNA was extracted and amplified for either the AAV vector using primers RPSP and DLASP or for β-globin. Amplification of β-globin served as a control for template integrity. The number of colonies showing vector specific bands from the total number containing B-globin signals provided the transduction efficiency. For HIV A, copy number corresponded to 12, 120 and 1200 copies of the genome. For β-globin, copy number controls showed amplification from 80, 160 and 1,000 cells.

Assays to test for LTC-IC colonies were performed 5, 8 and 12 weeks after culture initiation by inoculation of suspension cells from LTBMC into methylcellulose medium (Stem Cell Technologies, Vancouver, BC). Cells were harvested from LTBMC by trypsinization, washed and resuspended in 500 µl Iscove's modified Dulbecco's Medium (IMDM) with 30% heat-inactivated FBS (Gibco, Grand Island, N.Y.) and L-glutamine. The cell suspensions were mixed with a suspension containing 0.4% methylcellulose (MethoCult, Stem Cell Technologies, Inc.), 30% FCS, 1% bovine serum albumin, $10^{-4}$ M β-mercaptoethanol, 2 mM L-glutamine, 10 ng/ml IL-3 (R&D Systems, Minneapolis, Minn.), 50 ng/ml GM-CSF (R&D Systems), 50 U/ml erythropoietin (Amgen, Thousand Oaks, Calif.) and placed in 12-well plates at a concentration of 10,000 cells per well per duplicate.

Colonies containing greater than 50 cells approximately 14 days after plating were scored microscopically. Individual colonies were plucked and washed. DNA was extracted from colonies by standard methods following RNase treatment, SDS-proteinase K digestion, phenol:chloroform extraction and ethanol precipitation. DNA extracted from each colony was resuspended in 25 µl 10 mM Tris buffer containing 1 mM EDTA (TE). Vector sequences and the human 0-globin gene from individual colonies were amplified by PCR as described above, followed by quantitation of the total number of vector-positive colonies also showing a positive signal for β-globin.

To determine transduction efficiencies of clonogenic cells in long term cultures, individual colonies harvested from LTC-IC (LTBMC) were analyzed. Entire LTBMC wells were harvested following trypsonization of stromal layers from cultures initiated with vCWRHIVAPAP-transduced and untransduced cells, washed and placed in LTC-IC assays at 5, 8 and 10 weeks after transduction. Colonies developing from LTC-IC were primarily CFU-GEMM (colony forming units granulocute, erythroid, monocyte, macrophage) and CFU-GM; a few CFU-G, CFU-M and BFU-E were also observed.

Individual colonies were plucked from the methylcellulose in LTC-IC assays, and DNA was extracted and analyzed for the presence of vector sequences by amplification of the HIV LTR antisense gene using primers RPSP and DLASP.

The LTC-IC assays were performed as follows. Cells were harvested by trypsinization, washed and plated in 12-well plates at 2–3×$10^4$ cells/cm$^2$ in cRPMI. The stroma were irradiated with 15 Gray 250 KVp X-ray when a confluency of approximately 70% was reached. Medium was removed and the plates were overlaid with CD34 cells in long-term culture medium (Myelocult ("Stem" Cell Technologies, Vancouver, BC) containing 1 μM hydrocortisone (Sigma) and 100 μ/ml penicillin plus 100 mg/ml streptomycin) at a density of 2–6×10$^4$ cells/cm$^2$ either with or without the addition of vCWRHIVAPAP at a functional MOI of 2–3 (particle MOI:400–600). Suspension cells were washed after 24–48 hours and replated on washed stromal layers. Cultures were maintained by demi-depopulation of cells every 7–10 days.

For most donors, a high percentage of week 5 LTC-IC colonies had intact DNA (at varying quantities). β-globin controls indicated that the DNA template was inadequate in some cells lacking intact DNA. At weeks 8 and 10, LTC-IC colonies still showed vector specific signals in the absence of selective pressure, indicating stable transduction. The inventive method tHus can result in stable transduction, in vitro, for 5, 8 or 10 weeks, or longer. Free vector DNA was undetectable in the cultures, indicating that the vector signals observed in transduced LTC-IC colonies originated from transduced cells.

Tables 5 and 6 show data from LTC-IC assays of bone marrow CD34$^{+++}$CD38$^-$ and G0CD34 cells, and give the total number of LTC-IC colonies observed in 5, 8 and 12 week cultures, along with the percentage of vector positive colonies. The data show that the method successfully transferred the DNA to highly primitive multi-potential hematopoietic stem cells which have previously been recalcitrant to transfection.

TABLE 5 vCWRHIVAPAP Sequences in Individual Colonies from LTC-IC Assays; Bone Marrow CD34$^{+++}$CD38$^-$ Cells

| DONOR | WEEK 5 LTC-IC | | WEEK 8 LTC-IC | | WEEK 12 LTC-IC | |
|---|---|---|---|---|---|---|
| | vector + colonies | total colony number | vector + colonies | total colony number | vector + colonies | total colony number |
| OM | 25%(5/20) | 762 | 15%(3/20) | 45 | 40% (4/10) | 10 |
| RL | 20%(4/20) | 185 | 10%(2/20) | 90 | 0% (0/4) | 4 |
| RS | 20%(4/20) | 144 | 18%(3/17) | 17 | 50% (8/16) | 16 |
| ME | 10%(2/20) | 30 | 25%(3/12) | 12 | N.A. | N.A. |
| LA | 5%(1/20) | 393 | 15%(3/20) | 24 | N.A. | N.A. |
| CL | N.D. | N.D. | | 193 | 14 | |
| ES | | 150 | | | 7 | 6 |

TABLE 6

VCWRHIVAPAP Sequences in Individual Colonies from LTC-IC Assays; Bone Marrow G0CD34 Cells

| DONOR | WEEK 5 LTC-IC | | WEEK 8 LTC-IC | | WEEK 12 LTC-IC | |
|---|---|---|---|---|---|---|
| | vector + colonies | total colony number | vector + colonies | total colony number | vector + colonies | total colony number |
| JG | 15%(3/20) | 137 | 24%(4/17) | 17 | N.A. | N.A. |
| DP | 50% (10/10) | 175 | 30%(3/10) | 10 | 15% (3/20) | 20 |
| AA | 20%(4/20) | 344 | 11%(1/9) | 9 | 25% (1/4) | 4 |
| SM | 10%(2/20) | 42 | 36%(4/11) | 11 | 25% (1/4) | 4 |
| AS | 50% (10/20) | 111 | 36%(4/11) | 11 | 38% (3/8) | 8 |

The data from the LTC-IC assays indicated that the population of G0 CD34 cells contain more primitive progenitor cells than do G1 CD34 cells. The AAV vectors of the present invention notably were capable of transducing LTC-IC of a very primitive population of hematopoietic stem cells. Vector sequences were detected in extended LTC-IC at 8 and 12 weeks post transduction, indicating highly stable gene transfer. Importantly, AAV vector transduction was observed in the absence of selective pressure. Transduced cells had activity for more than 60 days in culture. Thus, AAV vectors integrated at a reasonable frequency in non-dividing cells, unlike prior art methods which result in very low frequencies of integration.

The data in Tables 5 and 6 indicate stable gene transfer at least up to 12 weeks. Similar frequencies of integrated vector were observed when cells were transduced while in both G0 and G1, and the integration level remained comparable over the eight week period of study in multiple patients, showing stability of integration.

Heterologous stromal layers for long term bone marrow cultures were established by plating 5–10×10$^6$ allogeneic bone marrow mononuclear cells in T75 flasks in (cRPMI) RPMI 1640 with 10% fetal bovine serum (FBS) and L-glutamine. Stromal layers developed in 2–3 weeks and were used for long term culture initiating cell (LTC-IC) assays after at least three passages.

The integration status of vector genomes in transduced cells was analyzed by FISH. For FISH analysis of vCWRHIVAPAP transduced bone marrow CD34$^+$ and CD34$^+$38$^-$ cells in long term culture, CD34$^+$ or flow-sorted CD34$^+$38$^-$ cells were transduced with vCWRHIVAPAP at MOI:3 (particle MOI:600) immediately after isolation and placed in culture. Flow-sorted G0 CD34 and CD34$^{+++}$CD38$^-$ cells were transduced with vCWRHIVAPAP vector (particle MOI:1500/infectious MOI:15) over a period of 48 hours. The transduced cells were washed extensively and cultured in low cytokine concentrations (10 ng/ml IL-3, 10 ng/ml IL-6 and 1 ng/ml SCF). Aliguots from the culture then were placed in medium with increased cytokine concentrations (50 ng/ml IL-3, 50 ng/ml IL-6 and 5 ng/ml SCF) for FISH analysis at different time points.

FISH analysis was performed as described in Fisher Adams et al., *Blood* 88:492, 1996. Briefly, at the time of analysis, suspension cells were harvested from cultures as described above. The cells were washed and resuspended in fresh IMDM containing 20% FCS, 2 mM L-glutamine, 50 ng/ml IL-3, 50 ng/ml IL-6 and 5 ng/ml stem cell factor for 72 hours to boost the mitotic index. To block cells in metaphase, cells were placed in fresh cytokine-containing medium with colcemid (0.025 mg/ml) for 16 to 24 hours. Harvested cells were treated with a hypotonic solution (0.4% KCL and fixed in a 3:1 methanol: acetic acid solution prior to dropping on slides to obtain nuclear spreads.

A 3.6 kb Hpa1-SnaB1 fragment from pCWRHIVASVN was labeled with digoxygenindeoxyuridine triphosphate by nick translation and used as a probe for FISH. The probe was derived from CWRHIVASVN rather than CWRHIVAPAP to avoid PLAP detection of the endogenous human PLAP gene while still providing a large enough fragment for use as an efficient FISH probe. See FIG. 7 for the placement of the probe in relation to the vector. The probe was specific for the RSV LTR, antisense to HIV-1, the polyadenylation region and the neomycin phosphotransferase gene under the control of the SV40 promoter and hybridized to vCWRHIVAPAP and vCWRHIVASVN transduced cells with equivalent efficiency. A BamHI fragment from AAVS1 (kindly provided by R. Kotin, NIH) was used to probe for the chromosome 19 AAVSI site. Hybridization and washes were performed as described in the ONCOR Capitol Chromosome in situ Hybridization System Handbook (1994). Visualization and imaging was achieved using a PSI imaging system (Perceptive Scientific Instruments Inc., League City, Tex.). At least 100 nuclear spreads were scored for each sample (except HJ where there were fewer suspension cells for analysis.

Cells generally were harvested at 2–10 weeks post transduction to assess the stability of integration. Only metaphase spreads showing signals on both sister chromatids were scored as positive. Interphase spreads which could contain either integrated or episomal copies of vector genomes were also followed over time. Results demonstrated stable gene transfer into primitive, quiescent hematopoietic stem/progenitor cells.

TABLE 7

Percentage of Individual G0CD34 and G1CD34 Colonies from LTC-IC Assays Containing vCWRHIVAPAP Sequences

| DONOR | WEEK 5 LTC-IC | | WEEK 8 LTC-IC | | WEEK 12 LTC-IC | |
|---|---|---|---|---|---|---|
| | G0 | G1 | G0 | G1 | G0 | G1 |
| JG | 15% | 24% | 18% | 0% | N.A. | N.A. |
| DP | 50% | 30% | 20% | 20% | 15% | N.A. |
| AA | 20% | 11% | 19% | 86% | 25% | 14% |
| SM | 10% | 36% | 50% | N.D. | 25% | N.D. |
| AS | 50% | 36% | 25% | N.D. | 38% | N.D. |

Table 7 provides the relative number of individual G0 CD34 and G1 CD34 colonies from LTC-IC assays which contained vCWRHIVAPAP sequences. Table 8 provides the percentage of individual $CD34^+CD38^-$ colonies from related LTC-IC assays which contained vCWRHIVAPAP sequences. Cells were harvested at the indicated timepoints post-transduction to assess the stability of integration. Interphase spreads, which could contain either integrated or episomal copies of vector genomes, were also followed over time.

To determine if AAV vector genomes could integrate into the more primitive hemagglutinating fraction of CD34 cells, we analyzed cultures initiated with bone marrow cells by FISH.

TABLE 8

FISH Analysis of vCWRHIVAPAP-Transduced Bone Marrow $CD34^+CD38^-$ Cells

| Donor | Week Post-Transduction | + metaphase | + Interphase (<3 signals) | + Interphase (> signals) |
|---|---|---|---|---|
| OM | 4 | 9.4% (6/64) | 2.3% (7/278) | 7.5% (23/278) |
| | 6 | 8.1% (5/62) | 4.5% (17/307) | 14.1% (53/307) |
| | 8 | 10/0% (3/30) | 7.1% (20/242) | 6.4% (18/2242) |
| | 10 | 13.5% (5/37) | 11.8% (42/301) | 3.4% (12/301) |
| RL | 4 | 7.4% (4/54) | 3.3% (15/402) | 7.5% (34/402) |
| | 6 | 9.4% (5/53) | 2.9% (14/450) | 3.7% (18/450) |
| | 8 | 6.4% (3/47) | 5.8% (24/385) | 1.7% (7/385) |
| | 10 | 14.3% (4/28) | 5.8% (25/400) | 0.7% (3/400) |
| RS | 4 | 12.2% (5/41) | 7.6% (12/125) | 13.3% (21/125) |
| | 6 | 12.5% (6/42) | 11.5% (21/150) | 6.6% (12/150) |
| | 8 | 11.1% (4/36) | 12.2% (15/105) | 2.4% (3/105) |
| ME | 4 | 14.3% (4/28/) | 2.4% (4/165) | 10.9% (18/165) |
| | 6 | 13.9% (5/36) | 14.6% (38/260) | 5.4% (14/260) |
| | 8 | 12.2% (5/41) | 16.0% (26/162) | 3.1% (5/163) |
| | 10 | 9.3% (4/43) | 19.7% (42/213) | 3.8 (8/213) |
| LA | 4 | 10.6% (5/47) | 2.6% (6/201) | 11.5% (27/201) |
| | 6 | 10.5% (4/38) | 5.5% (14/255) | 9.4% (24/255) |
| | 8 | 10.6% (5/47) | 7.8% (15/192) | 1.0% (2/192) |
| | 10 | 9.1% (4/44) | 21.0% (45/214) | 2.8% (6/214) |
| CL | 4 | 8.8% (7/80) | 5.7% (18/318) | 6.9% (22/318) |
| | 6 | 13.6% (9/66) | 3.6% (15/414) | 5.6% (23/414) |
| | 8 | 11.1% (3/27) | 14.9% (57/382) | 3.7% (14/382) |
| ES | 6 | 13.8% (9/65) | 4.7% (18/385) | 1.3% (5/385) |
| | 10 | 16.3% (7/43) | 7.4% (23/312) | 2.2% (7/312) |

TABLE 9

FISH Analysis of vCWRHIVAPAP-Transduced Bone Marrow CD34+CD38- Cells

| Donor | Week Post-Transduction | + metaphase | + Interphase (<3 signals) | + Interphase (> signals) |
|---|---|---|---|---|
| JG | 2 | 30% (12/40) | 4.7% (11/183) | 26.8% (52/183) |
|    | 4 | 22.9% (8/35) | 6.0% (13/187) | 15.5% (31/187) |
|    | 6 | 20% (6/30)   | 8.5% (17/175) | 12.5% (24/175) |
|    | 8 | 15.2% (5/33) | 6.4% (15/201) | 14.8% (32/201) |
| DP | 2 | 11.1% (5/45) | 9.5% (19/50)  | 29.8 (50/149) |
|    | 4 | 13.6% (8/59) | 9.4% (50/422) | 11.1% (59/422) |
|    | 6 | 8.8% (5/57)  | 7.8% (16/163) | 12.7% (26/163) |
|    | 8 | 9.1% (3/30)  | 14.8% (38/208)| 3.9% (10/208) |
| AA | 2 | 17.1% (7/41) | 20.4% (48/180)| 3.0% (7/180) |
|    | 4 | 11.8% (8/68) | 9.4% (50/422) | 11.1% (59/422) |
|    | 6 | 14.0% (8/57) | 5.4% (28/419) | 13.9% (72/419) |
|    | 8 | 11.1% (6/54) | 10.3% (46/341)| 13.2% (59/341) |
| SM | 4 | 12.1% (11/91)| 4.6% (12/284) | 8.6% (28/284) |
|    | 6 | 11.1% (6/54) | 10.8% (27/208)| 6.0% (15/208) |
|    | 8 | 30% (5/30)   | 14.4% (30/175)| 1.9% (4/175 |
| AS | 4 | 15.3% (11/72)| 3.8% (12/282) | 7.3% (23/282) |
|    | 6 | 12.8% (5/39) | 3.8% (15/351) | 7.6% (30/351) |
|    | 8 | 30% (4/44)   | 11.3% (15/112)| 4.5% (6/112) |

The data contained in Tables 8 and 9 (FISH analyses) demonstrate that stable gene transfer into highly primitive quiescent hematopoietic stem/progenitor cells was achieved. It is clear that both bone marrow CD34+CD38- cells and bone marrow G0CD34 cells shared similar functional capacities: both contained LTC-IC with extended clonogenic abilities, indicating residence in G0/preservation of non-dividing status. Both populations had extended replating abilities with metaphases observed to 8 or 10 weeks. The CD34+CD38- cells represented a more quiescent and more homogeneous cell population than G0 cells isolated by DNA and RNA standing alone., The CD34+++CD38- cells remained non-dividing for at least 2 days and the majority remained non-dividing after seven days, in the presence of cytokines. AAV vector transduction of both populations resulted in stable integration of the vector genome up to 10 weeks. Some donor to donor variability was observed in the frequency of transduction, possibly due to polymorphisms in the receptors. These results suggest that AAV vectors can stably transduce subpopulations of CD34+++ cells that are highly enriched for primitive, quiescent progenitors and which have previously been shown to be difficult or impossible to genetically modify.

AAV vectors are able to transduce CD34+38- cells engraft efficiently in immune deficient NOD/SCID mice in a multilineage long lived fashion. These very primitive human hematopoietic stem cells engrafting in NOD/SCID mice or SCID repopulating cells (SRC) have also been shown to be very difficult to genetically modify. AAV-transduced CD34+38 cells engraft and give rise to long lived CD34 cells as well as myeloid (CD14) and B lymphoid (CD19) cells. The latter differentiate from transduced CD34+38- progenitor cells. Importantly, long lived clonogenic cells in marrow of NOD/SCID mice were also found to be transduced by AAV vectors, demonstrating that AAV vectors transduce very primitive stem cells capable of in vivo hematopoiesis in a model system for human gene therapy. See Example 3.

The methods and vectors of this invention may be used to transduce hematopoietic stem cells in the G0 phase of the cell cycle, although cells not in G0 may be transduced as well. Such cells can be used to treat a number of diseases, including inherited diseases such as adenosine deaminase deficiency, lysosomal storage diseases, thalassemia, sickle cell disease and glucocerebrosidase deficiency, oncogenic processes and cancer, viral infections such as HIV infection, atherosclerosis and other cardiovascular diseases, blood diseases etc. Any DNA may be transferred to hematopoietic cells by this method, however, DNAs of particular relevance include genes expressing blood factors, HIV antisense DNA or any useful gene or gene fragment, including genes inserted merely for a reporter function.

Antisense genes advantageously may be transferred to hematopoietic cells by the inventive methods. Those of skill in the art will readily appreciate that many different adeno-associated virus vectors may be used with the inventive methods. Such vectors desirably have the following characteristics: the DNA to be transferred is contained within the AAV ITRs and the vector is encapsidated. The following non-limiting examples are provided to illustrate the invention.

EXAMPLES

Example 1

Production and Preparation of AAV Vectors

All AAV vectors were derived from the base vector CWRSV, which contains bases 1–189 and 4045–4680 of wild type AAV2, including the 5' and 3' ITR and the indigenous AAV2 polyadenylation signal. CWRHIVASVN contains two transcriptional cassettes, one encoding the neomycin phosphotransferase ($NEO^R$) gene under SV40 early promotor control and the other encoding an antisense transcript complimentary to HIV-1 LTR sequences under (RSV LTR) control. CWRHIVAPAP is identical to CWRHIVASVN except for the substitution of a gene cassette encoding the thermostable human placental alkaline phosphatase (PLAP) gene under phosphoglycerate kinase (PGK) promotor control for the SVNeo cassette. See FIG. 7 for a map of the vectors.

The recombinant virus vectors vCWRHIVASVN, vCWRHIVAPAP and vCWRAP were encapsidated using HSV-1MP17 as helper viruses according to prior art methods. Briefly, semiconfluent 293 cells were infected with HSV-1 MP17, (multiplicity of infection (MOI):0.1) and transfected one hour postinfection with 20 μg of the vector plasmids by calcium phosphate co-precipitation (CellPhect, Pharmacea Biotech, Sweden). AAV-encoded rep (DNA replication) and cap (capsid proteins) gene functions were provided in trans. Cells were harvested 72 hours post-transfection and lysed by three cycles of freeze-thawing and sonication. Vector stocks were treated with 400V DNase I (Boehringer Mannheim) per $10^7$ cells, to digest residual plasmid and cellular DNA. The lysate was digested with 0.25% trypsin and 1% sodium deoxycholate for 30-minutes at 37° C. before further purification on two rounds of isopycnic cesium chloride (density: 1.41 g/ml) gradient centrifugation for 64 and 48 hours, respectively, at 40,000 rpm. Fractions (0.5 to 1 ml) were collected and density was measured with a refractometer.

Particle titers were determined by dot blot analysis. DNA was isolated from each fraction by standard procedures following proteinase K digestion, phenol and phenol:chloroform extractions and ethanol precipitation. DNA was dot blotted onto nitrocellulose and hybridized with a vector specific probe (BamHI-SnaBI fragment of CWRHIVAPAP, see FIG. 7). Duplicate blots were hybridized with a wild type AAV specific probe (SacII fragment of pTZAAV). Results were analyzed on a phosphorimager and titers determined from standard curves. pBluescript DNA served as a negative control. A particle titer of $10^9$/ml was obtained for vCWRHIVAPAP and $10^8$/ml for vCWRHIVASVN.

The functional titers of vCWRHIVAPAP and vCWRHIVASVN stocks were determined by quantitation of specific alkaline phosphatase expressing cells and $NEO^R$ colonies following serial dilutions on 293 cells. The presence of the full length of vector genomes and the absence of contaminating wild type AAV was confirmed by either dot blot or electrophoretic analysis of DNA extracted from vector stocks, followed by Southern hybridization with vector and wild type specific probes. All helper virus stocks and cell lines were screened for and found to be free of wild type AAV contamination.

Example 2

Transduction of CD34 Cells and $CD34^{+++}CD38^-$ Cells

Transductions with vCWRHIVAPAP were performed at functional MOI:1-3 and with vCWRHIVASVN at MOI:0.1-0.2 unless otherwise noted. Cells were transduced immediately upon isolation at the time of culture initiation at 37° C. in a humidified, $CO_2$ incubator. Transductions were performed by the direct addition of vector to cells at functional MOIs of 1-10 (corresponding to particle MOIs of 200-2000) and left undisturbed for about 24 to about 48 hours, following which time cells were washed and replated. The washes performed were sufficient to remove all detectible free vector left in the medium. Two batches of vCWRHIVAPAP of equivalent titer and one batch of vCWRHIVASVN were used for all examples reported here. CD34 cells were transduced with vCWRHIVAPAP at MOI:1-2 (particle MOI: 200-600) immediately upon isolation at the time of culture initiation.

Example 3

AAV Vector Transduction of Primitive In Vivo Repopulating Cells

Low density marrow mononuclear cells were separated from fresh umbilical cord blood samples by Ficoll-Hypaque (Pharmacia) gradient centrifugation. Cells were washed three times in phosphate-buffered saline (PBS) supplemented with 5% FCS and the cell viability was estimated using trypan blue staining. Purification of $CD34^+$ cells was performed using immunomagnetic MACS column separation according to the manufacturer's protocol (Miltenyi Biotec). Cells were passed through two columns to enrich for $CD34^{+++}$ cells. Enriched CD34 cord blood cells were labeled with HPCA-2 anti-CD34 FITC-conjugated (Becton Dickinson) and anti-CD38 PE-conjugated (Becton Dickinson) antibodies as recommended by the manufacturer. Direct immunofluorescence staining was performed to sort the dimmest 20% of the $CD34^{+++}CD38^-$ population on a Mo-Flo high speed flow cytometer.

Sorted $CD34^{+++}CD38^-$ cells were washed shortly after isolation and cultured in IMDM containing 20% FCS, IL-6 (10 ng/ml), IL-3 (10 ng/ml) and SCF (1 ng/ml) in either 6 or 12-well plates. Transductions were performed immediately upon culture initiation by direct addition of sonicated vector stocks at a particle MOI of ~400 (infectious MOI:4) into 2 ml of culture media. Cells were then replaced into the incubator and cultured at 37° C. in humidified 5% $CO_2$. Cells were washed three times with PBS 34 hours post-transduction. Between 30,000 and 70,000 transduced $CD34^{+++}CD38^-$ cells were resuspended in 200 µl PBS for delivery into NOD/SCID mice by tail vein injection.

What is claimed is:

1. A method for stably transferring DNA into multi-potential hematopoietic stem cells in the G0 phase of the cell cycle, which comprises transducing said multi-potential hematopoietic stem cells with an adeno-associated virus vector that contains said DNA, wherein the transferred DNA remains integrated into the genome of the multi-potential hematopoietic stem cells for at least 4 weeks, wherein the multi-potential hematopoietic stem cells are maintained in the presence of cytokines IL-3, IL-6 and stem cell factor, and wherein the levels of said cytokines are about 10 ng/ml IL-3, about 10 ng/ml IL-6 and 1 ng/ml stem cell factor.

2. A method according to claim 1, wherein the transduced multi-potential hematopoietic stem cells are maintained under conditions such that at least about 92 to 99% of the cells in the G0 phase remain in the G0 phase for at least about two days.

3. A method according to claim 2, wherein the conditions under which the transduced multi-potential hematopoietic stem cells are maintained include a transduction time of about 2 hours to about 48 hours.

4. A method according to claim 2, wherein the conditions under which the transduced multi-potential hematopoietic stem cells are maintained include a transduction time of about 2 hours to about 24 hours.

5. A method according to claim 2, wherein the conditions under which the transduced multi-potential hematopoietic stem cells are maintained include a transduction time of about 18 hours to about 24 hours.

6. A method according to claim 1, wherein the transferred gene remains integrated into the genome of the multi-potential hematopoietic stem cells for at least 8 weeks.

7. A method according to claim 1, wherein the multi-potential hematopoietic stem cells are $CD34^{+++}CD38^-$ cells.

8. A method according to claim 1, wherein the adeno-associated virus vector contains said DNA within the adeno-associated virus inverted terminal repeats, and wherein the adeno-associated virus vector is encapsidated.

9. A method according to claim 8, wherein the adeno-associated virus vector has a wild-type polyadenylation region.

10. A method according to claim 8, wherein the adeno-associated virus vector has a heterologous polyadenylation region.

11. A method according to claim 1, wherein the DNA is selected from a gene, a gene fragment, an antisense DNA, a marker gene, a reporter gene and a recombinant DNA.

* * * * *

UNITED STATES PATENT AND TRADEMARK OFFICE
CERTIFICATE OF CORRECTION

| | | |
|---|---|---|
| PATENT NO. | : 6,919,209 B1 | Page 1 of 2 |
| DATED | : July 19, 2005 | |
| INVENTOR(S) | : Saswati Chatterjee et al. | |

It is certified that error appears in the above-identified patent and that said Letters Patent is hereby corrected as shown below:

<u>Title page,</u>
Item [56], References Cited, OTHER PUBLICATIONS, "All et al." should read -- Ali et al. --.

<u>Column 6,</u>
Line 4, "e.g." should read -- i.e. --.
Line 56, after "in particular" delete comma.

<u>Column 7,</u>
Line 1, after "(GMCSF)" insert -- ) --.
Line 27, delete "CWRHIVASVA".

<u>Column 8,</u>
Line 42, "were" should read -- was --.

<u>Column 10,</u>
Line 48, "19-50%" should read -- 10-50% --.
Line 55, "1992 & U.S." should read -- et al., <u>Science</u> 258:1485-1488 (1992); United States Patent No. --.

<u>Column 12,</u>
Line 43, "0-globin" should read -- β-globin --.
Line 56, "granulocute" should read -- granulocyte --.
Line 57, "BFU-E" should read -- CFU-E --.

<u>Column 13,</u>
Line 17, "tHus" should read -- thus --.

<u>Column 14,</u>
Lines 56-57, "Fisher Adams" should read -- Fisher-Adams --.

<u>Column 15,</u>
Line 5, delete "PLAP".

<u>Column 16,</u>
Table 8, under the Donor "ME", at the metaphase column "(4/28/)" should read -- (4/28) --.

UNITED STATES PATENT AND TRADEMARK OFFICE
CERTIFICATE OF CORRECTION

PATENT NO.   : 6,919,209 B1
DATED        : July 19, 2005
INVENTOR(S)  : Saswati Chatterjee et al.

It is certified that error appears in the above-identified patent and that said Letters Patent is hereby corrected as shown below:

Column 17,
Table 9, under the Donor "SM", at the interphase column for (>signals), "(4/175" should read -- (4/175) --.
Line 52, "have also" should read -- also have --.

Column 19,
Line 2, "Pharmacca" should read -- Pharmacia --.

Signed and Sealed this

Second Day of May, 2006

JON W. DUDAS
*Director of the United States Patent and Trademark Office*